United States Patent
Colman et al.

(10) Patent No.: US 10,070,826 B2
(45) Date of Patent: Sep. 11, 2018

(54) METHODS, APPARATUS AND SYSTEMS FOR MONITORING $CO_2$

(71) Applicant: ORIDION MEDICAL 1987 LTD., Jerusalem (IL)

(72) Inventors: Joshua Lewis Colman, Jerusalem (IL); Iris Shalev Stein, Mattan (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 199 days.

(21) Appl. No.: 14/176,045

(22) Filed: Feb. 8, 2014

(65) Prior Publication Data

US 2014/0155775 A1    Jun. 5, 2014

Related U.S. Application Data

(63) Continuation of application No. 12/994,614, filed as application No. PCT/IL2009/000538 on May 31, 2009, now Pat. No. 9,706,965.
(Continued)

(51) Int. Cl.
*A61B 5/08* (2006.01)
*A61B 5/00* (2006.01)
(Continued)

(52) U.S. Cl.
CPC .......... *A61B 5/7282* (2013.01); *A61B 5/0205* (2013.01); *A61B 5/082* (2013.01);
(Continued)

(58) Field of Classification Search
CPC ...... A61M 2230/005; A61M 2230/432; A61M 16/04; A61M 16/0486; A61M 16/00;
(Continued)

(56) References Cited

U.S. PATENT DOCUMENTS

| | | |
|---|---|---|
| 4,270,530 A | 6/1981 | Baum |
| 4,537,190 A | 8/1985 | Caillot |

(Continued)

FOREIGN PATENT DOCUMENTS

| | | |
|---|---|---|
| EP | 0850652 | 7/1998 |
| WO | 99/20332 | 4/1999 |

(Continued)

OTHER PUBLICATIONS

Badgwell, J. M. et al., (1987) End-tidal PCO2 measurements sampled at the distal and proximal ends of the endotracheal tube in infants and children. Anesth Analg 66(10):959-64.
(Continued)

*Primary Examiner* — Patricia Mallari
*Assistant Examiner* — Karen Toth

(57) ABSTRACT

There is provided herein methods, apparatus and systems for evaluating carbon dioxide ($CO_2$) concentration in a subject's breath, for example in subjects ventilated with High Frequency Ventilation (HFV), the method includes inserting to a trachea of a subject an endotrachial tube (ETT), sampling breath from an area in the trachea located in proximity to a distal end of the endotrachial tube (ETT) and evaluating one or more $CO_2$ related parameters of the sampled breath.

11 Claims, 7 Drawing Sheets

Related U.S. Application Data

(60) Provisional application No. 61/071,959, filed on May 28, 2008.

(51) Int. Cl.

| | | |
|---|---|---|
| *A61M 16/08* | (2006.01) | |
| *A61B 5/0205* | (2006.01) | |
| *A61B 5/083* | (2006.01) | |
| *A61B 5/097* | (2006.01) | |
| *A61M 5/172* | (2006.01) | |
| *G06N 5/04* | (2006.01) | |
| *A61M 16/04* | (2006.01) | |
| *A61M 16/00* | (2006.01) | |
| *A61M 16/10* | (2006.01) | |
| *A61B 5/021* | (2006.01) | |
| *A61B 5/024* | (2006.01) | |
| *A61B 5/0402* | (2006.01) | |
| *A61B 5/0476* | (2006.01) | |
| *A61B 5/087* | (2006.01) | |

(52) U.S. Cl.
CPC ............ *A61B 5/0836* (2013.01); *A61B 5/097* (2013.01); *A61B 5/7246* (2013.01); *A61B 5/7264* (2013.01); *A61B 5/742* (2013.01); *A61B 5/746* (2013.01); *A61M 5/1723* (2013.01); *A61M 16/0057* (2013.01); *A61M 16/0069* (2014.02); *A61M 16/04* (2013.01); *A61M 16/0463* (2013.01); *A61M 16/0484* (2014.02); *A61M 16/0486* (2014.02); *A61M 16/0488* (2013.01); *A61M 16/085* (2014.02); *A61M 16/0816* (2013.01); *A61B 5/021* (2013.01); *A61B 5/024* (2013.01); *A61B 5/0402* (2013.01); *A61B 5/0476* (2013.01); *A61B 5/087* (2013.01); *A61B 5/0816* (2013.01); *A61B 5/0833* (2013.01); *A61M 16/0096* (2013.01); *A61M 2016/0413* (2013.01); *A61M 2016/103* (2013.01); *A61M 2230/432* (2013.01); *G06N 5/04* (2013.01)

(58) Field of Classification Search
CPC .......... A61M 16/0096; A61M 2230/43; A61B 5/0836; A61B 5/082; A61B 5/097; A61B 5/08
See application file for complete search history.

(56) References Cited

U.S. PATENT DOCUMENTS

| | | | |
|---|---|---|---|
| 4,584,998 | A | 4/1986 | McGrail |
| 5,101,817 | A | 4/1992 | Etter |
| 5,193,544 | A | 3/1993 | Jaffe |
| 5,235,970 | A | 8/1993 | Augustine |
| 5,246,012 | A | 9/1993 | Strickland |
| 5,313,939 | A | 5/1994 | Gonzalez |
| 5,355,893 | A | 10/1994 | Mick |
| 5,636,625 | A | 6/1997 | Miyagi |
| 5,669,380 | A | 9/1997 | Garry |
| 5,906,204 | A | 5/1999 | Beran |
| 5,954,050 | A | 9/1999 | Christopher |
| 6,098,617 | A | 8/2000 | Connell |
| 6,273,728 | B1 * | 8/2001 | van Meurs ............ G09B 23/28 434/262 |
| 6,694,978 | B1 * | 2/2004 | Bennarsten ....... A61M 16/0096 128/203.24 |
| 2005/0085799 | A1 * | 4/2005 | Luria .................. A61B 5/6803 606/1 |
| 2005/0279360 | A1 | 12/2005 | Wei |
| 2006/0004297 | A1 | 1/2006 | Orr |
| 2007/0144518 | A1 * | 6/2007 | Acker .................. A61B 5/0836 128/204.21 |
| 2008/0072905 | A1 | 3/2008 | Baker |
| 2008/0154250 | A1 | 6/2008 | Makower |
| 2008/0295839 | A1 * | 12/2008 | Habashi ............ A61M 16/0051 128/204.22 |
| 2013/0133655 | A1 * | 5/2013 | Kimm ................ A61M 16/0057 128/204.23 |
| 2016/0228661 | A1 * | 8/2016 | Larsson ............... A61B 5/0488 |

FOREIGN PATENT DOCUMENTS

| | | |
|---|---|---|
| WO | 99/29358 | 6/1999 |
| WO | 2005/107839 | 11/2005 |
| WO | 2007/020639 | 2/2007 |
| WO | 2008/014412 | 1/2008 |

OTHER PUBLICATIONS

Bhende, M. S. et al., (2001) End-tidal carbon dioxide monitoring in pediatrics—clinical applications. J Postgrad Med 47(3):215-8.

Bland, J. M. and Altman, Douglas G. (1986) Statistical methods for assessing agreement between two methods of clinical measurement. Lancet 1:307-10.

Colman, Yehoshua and Krauss, Baruch (1999) Microstream capnography technology: a new approach to an old problem. J Clin Monit 15(6):403-9.

Fujimoto, Shinji et al., (1994) Hypocarbia and cystic periventricular leukomalacia in premature infants. Arch Dis Child 71(2):F107-10.

Garland, Jeffrey S. (1995) Hypocarbia before surfactant therapy appears to increase bronchopulmonary dysplasia risk in infants with respiratory distress syndrome. Arch Pediatr Adolesc Med 149(6):617-22.

Hagerty, Jhon J. et al., (2002) Accuracy of a new low-flow sidestream capnography technology in newborns: a pilot study. J Perinatol 22(3):219-25.

Hand, Ivan L. et al., (1989) Discrepancies between transcutaneous and end-tidal carbon dioxide monitoring in the critically ill neonate with respiratory distress syndrome. Crit Care Med 17(6):556-9.

Kirpalani, H. et al., (1991) Technical and clinical aspects of capnography in neonates. J Med Eng Technol 15(4-5):154-61.

McEvedy, Bryony A. B. (1990)End-tidal carbon dioxide measurements in critically ill neonates: a comparison of side-stream and mainstream capnometers. Can J Anaesth 37(3):322-6.

McEvedy, B. A. B. et al., (1988) End-tidal, transcutaneous and arterial PCO2 measurements in critically ill neonates: a comparative study. Anesthesiology 69(1):112-6.

Palmisiano, Barbara W. et al., (1990) Transcutaneous PCO2 and PO2: a multicenter study of accuracy. J Clin Monitor 6:189-195.

Pascucci, Robert C. et al., (1989) Comparison of sidestream and mainstream capnometer in infants. Crit Care Med 17(6):560-562.

Proquitté, H. et al,. (2004) Current limitations of volumetric capnography in surfactant-depleted small lungs. Pediatr Crit Care Med 5(1):75-80.

Rennie, J. M. (1990) Transcutaneous carbon dioxide monitoring. Arch Dis Child 65:345-346.

Rozycki, Henry J. et al., (1998) Mainstream end-tidal carbon dioxide monitoring in the neonatal intensive care unit. Pediatrics 101(4 Pt 1):648-53.

Schieber, Richard A. et al., (1985) Accuracy of expiratory carbon dioxide measurements using the coaxial and circle breathing circuits in small subjects. J Clin Monit 1(3):149-55.

Sivan, Yakov et al., (1992) Estimation of arterial carbon dioxide by end-tidal and transcutaneous PCO2 measurements in ventilated children. Pediatr Pulmonol 12(3):153-7.

Strauss, Ronald G. (1991) Transfusion therapy in neonates. Am J Dis Child 145(8):904-11.

Tingay, D. G. et al., (2005) Monitoring of end tidal carbon dioxide and transcutaneous carbon dioxide during neonatal transport. Arch Dis Child Fetal Neonatal Ed 90(6):F523-F526.

Van De Bor, Margot et al., (1986) Perinatal factors and periventricular-intraventricular hemorrhage in preterm infants. Am J Dis Child 140(11):1125-30.

(56) References Cited

OTHER PUBLICATIONS

Wu, Chia-Hua et al., (2003) Good estimation of arterial carbon dioxide by end-tidal carbon dioxide monitoring in the neonatal intensive care unit. Pediatr Pulmonol 35(4):292-5.

Wyatt, J. S. et al., (1991) Response of cerebral blood volume to changes in arterial carbon dioxide tension in preterm and term infants. Pediatr Res 29(6):553-7.

Wyllie, Jonathan and Carlo, Waldemar A. (2006) The role of carbon dioxide detectors for confirmation of endotracheal tube position. Clin Perinatol 33(1):111-9.

* cited by examiner

METHODS, APPARATUS AND SYSTEMS FOR MONITORING CO$_2$

RELATED APPLICATION DATA

This application is a continuation of U.S. application Ser. No. 12/994,614, filed Nov. 24, 2010 (published as US 2011/0098592), which is the U.S. National Stage of International Application No. PCT/IL2009/000538, filed May 31, 2009, which claims the benefit of U.S. Provisional Application No. 61/071,959, filed May 28, 2008, the contents of each of which are herein incorporated by reference in their entireties.

FIELD OF THE INVENTION

The invention generally relates to method and apparatus for monitoring carbon dioxide (CO$_2$) in breath.

BACKGROUND

Continuous noninvasive monitoring of carbon dioxide (CO$_2$) levels in infants, particularly in a Neonatal Intensive Care Unit (NICU), is considered very important mainly in order to protect subjects such as infants from the complications of hypocarbia (less than the normal level of carbon dioxide in the blood) and hypercarbia (more than the normal level of carbon dioxide in the blood) and to avoid extra blood sampling which may cause anemia, discomfort, and pain. Noninvasive monitoring of carbon dioxide (CO$_2$) levels typically refers to exhaled breath analysis also referred to as capnography.

Capnography is a common method of monitoring and optionally displaying the CO$_2$ level(s), CO$_2$ waveform(s) and/or other CO$_2$ related parameters, such as End Tidal CO$_2$ (EtCO$_2$), in exhaled breath. Capnography also provides information relating to cell metabolism, blood perfusion, alveolar ventilation and other body functions or conditions, and may enable real-time diagnosis of patho-physiological abnormalities as well as technical problems related to ventilation. In intubated subjects (such as patients) capnography is performed by sampling exhaled breath around the exit of the endotrachial tube (ETT) at a sampling region between the proximal end of the ETT (close to the subject's mouth) and the ventilator circuit. In intubated small children and infants, however, capnography is not commonly used since it does not consistently provide satisfactory results. One of the reasons for the lack of satisfactory results in small children, infants and/or neonates especially neonates, relates to the use of uncuffed endotrachial tubes (ETTs) during their ventilation. A cuff is an inflatable balloon on the outer surface of the ETT used to hold the ETT in place and to close off the ventilated air exiting the ETT at its distal end (towards the subject's lung) from escaping around the tube outwards. In case of small children and/or infants, and especially neonates, cuffed ETTs are generally not used due to the risk of perforating or otherwise harming the gentle membrane of their trachea. The use of uncuffed ETTs results in ventilated air escaping around the tube during inhalation. Although this can be compensated for by changing the ventilator parameters, a greater problem arises during breath sampling (both in mainstream and sidestream capnography) which depends on the exhaled breath returning back through the ETT towards the sampling region. The uncuffed ETT allows the exhaled breath to return between the ETT and trachea, and out through the mouth without returning back through the ETT towards the sampling region. This is further exaggerated, since with neonates the ETT internal diameter is very small, typically between 2.5 to 4 mm, which imposes a large restriction, enhancing further the possibility of exhaled breath escaping round the tube. The small volume of exhaled breath (which is only a fraction of the low tidal volumes of infants and neonates) that does manage to return back through the ETT is also diluted with clean ventilated air (often present in a "dead space" of the ETT) which leads to difficult breath sampling and erroneous CO$_2$ readings.

This problem is further enhanced in mainstream capnography, in which the required airway section is connected inline between the proximal end of the ETT (close to the subject's mouth) and the ventilator circuit. Thus, it adds more dead space, competes for tidal volume, and may also cause a kink in the ETT, especially in small premature infants. When a flow sensor is connected to the ETT, the use of mainstream capnography is even more cumbersome. There is thus a need in the art for methods, systems and apparatuses that would allow accurate CO$_2$ monitoring, particularly in small children, infants or neonates.

High Frequency Ventilation (HFV):

In addition to the problems discussed hereinabove, which relates to CO$_2$ monitoring, the ventilation itself, particularly in neonates, but also with children and adults, still suffers from significant difficulties. Some neonates cannot be adequately ventilated even with sophisticated conventional ventilation. Therefore respiratory insufficiency remains one of the major causes of neonatal mortality. Intensification of conventional ventilation with higher rates and airway pressures leads to an increased incidence of barotrauma. Especially, the high shearing forces resulting from large pressure amplitudes damage the lung tissue. High Frequency Ventilation (HFV) has been shown to resolve or at least ameliorate this issue in many cases.

High Frequency Ventilation (HFV) is a technique of ventilation that uses respiratory rates that greatly exceed the rate of normal breathing. There are three main types of HFV:
1) High frequency positive pressure ventilation (HPPV, rate 60-150 breaths/minute);
2) High frequency jet ventilation (HFJV, rate 100-600 breaths/minute); and
3) High frequency oscillatory ventilation (HFOV, rate 300-3000 breaths/minute).

During conventional ventilation direct alveolar ventilation accomplishes pulmonary gas exchange. According to the classic concept of pulmonary ventilation an amount of gas reaching the alveoli equals the applied tidal volume minus the dead space volume. At tidal volumes below the size of the anatomical dead space this model fails to explain gas exchange. Instead, considerable mixing of fresh and exhaled gas in the airways and lungs is believed to be the key to the success of HFV in ventilating the lung at such very low tidal volumes. Among the advantages of high frequency oscillatory ventilation as compared to either conventional positive pressure or jet ventilation is its ability to promote gas exchange while using tidal volumes that are less than dead space. The ability of HFV to maintain oxygenation and ventilation while using minimal tidal volumes allows minimization of barotrauma and thus reduces the morbidity associated with ventilation.

Currently, two of the most important values that determine the respiratory therapy, such as HFV, is the Blood Gas CO$_2$ (PaCO$_2$) and the SpO$_2$ (the amount of oxygen being carried by the red blood cell in the blood). In order to monitor the subject's gas concentration in the blood, however, a blood sample must be taken. Blood sampling involves pain, discomfort and risk of infection. Especially with neonates, since the volume of blood is very small, each blood test takes a measurable percentage of the neonate's blood. This dictates periodic blood transfusions, where each blood transfusion promotes a further danger to the neonate or other subject.

There is thus a need in the art for methods, systems and apparatuses that would permit and facilitate accurate measurement(s) of medical parameter(s) for the evaluation and control of HFV therapy in subjects, particularly, but not only, in small children, infants or neonates.

SUMMARY

This summary section should not be construed as limiting the invention to any features described in this summary section.

General Sampling in Neonatal Environment

Some embodiments of the invention are generally directed to a method and apparatus for monitoring breath carbon dioxide ($CO_2$) in subjects, particularly, but not limited to, small children and infants, from a position much closer to the bronchial tubes than the current sampling position. This type of $CO_2$ sampling and evaluation may also be referred to as a "distal $CO_2$ measurement".

As discussed hereinabove, the current sampling configuration is problematic since it involves sampling from an area close to subject's mouth and to the proximal end of the ETT, wherein $CO_2$ is mixed with ventilated air, which eventually leads to erroneous $CO_2$ readings. This is particularly problematic when using an uncuffed endotrachial tube (ETT), which is very common in small children, infants and neonates. It was found that sampling breath from a position at a lower section of the trachea closer to the bronchial tubes (distal $CO_2$ measurement) may be less susceptible to air leak and/or mixing of the measured $CO_2$ with inhaled air. More particularly, sampling breath for distal $CO_2$ measurement may be performed at the distal end of the ETT which is adapted to be positioned inside the bronchial tube. According to some embodiments, sampling breath for distal $CO_2$ measurement may be performed by inserting a catheter into the ETT, wherein the catheter is adapted to sample $CO_2$. According to some embodiments, sampling breath for distal $CO_2$ measurement may be performed by sampling breath through the second (extra) lumen (typically having a very small diameter compared to the main lumen) of a double lumen ETT.

Sampling in Subjects Treated with High Frequency Ventilation (HFV):

Additional or alternative embodiments of the invention are generally directed to a method and apparatus for using capnography in monitoring breath carbon dioxide ($CO_2$) in subjects, particularly, but not limited to, small children and infants, who are ventilated by High Frequency Ventilation (HFV) technique.

When considering capnography for replacing at least some of the blood gas samples, and in general to provide continuous monitoring for HFV (such as HFOV) mode of ventilation, some difficulties arise:

a) Capnographs are generally designed to detect breath cycles up to rates of about 120-150 breaths per minute. As mentioned above, with HFV, frequencies are much higher. A limiting factor being the response time, which even for the fastest capnograph systems is generally more than 100 msec, which is far too slow for this mode of ventilation. In addition, it is most probable, that even if one had a capnograph system that was faster and able to detect changes at frequencies similar to those of the HFV ventilation mode, no breath cycle would be seen Since the $CO_2$ is mainly diffusing out, and only ripples would be seen caused by the pressure fluctuations.

b) Capnographs are generally designed such that if a breath cycle (a minimal sinusoidal wave) is not detected, a "no breath" alarm is triggered.

c) More important, as mentioned herein the considerable mixing of fresh and exhaled gas in the airways and lungs creates a status where the $CO_2$ concentration along the subject's airway changes and decreases so that at the standard position for capnography sampling, either mainstream or sidestream, the concentration will be much lower than what is really occurring in the lungs. Hence, $CO_2$ as currently measured would not be comparative to the blood gas value, and even if it had some correlation, it would have very low resolution. It was found that the $CO_2$ concentrations at these standard positions to be about eight times lower than those measured for standard ventilation modes. It is also noted that since there is no breath cycle, the $CO_2$ concentration is also an average value without peaks.

According to some embodiments of the invention, there are provided a method and apparatus that may overcome one or more issues related to difficulties such as those discussed hereinabove, and to facilitate $CO_2$ sampling and monitoring in subjects (for example, but not limited to, children, infants, and neonates) ventilated by the HFV mode. According to some embodiments of the invention, there are provided a method and apparatus for $CO_2$ sampling and monitoring in subjects (but not limited to, children, infants, and neonates) ventilated by the HFV mode.

According to some embodiments of the invention, there is provided a method for evaluating concentration of carbon dioxide ($CO_2$) in a subject's breath, the method includes inserting an endotrachial tube (ETT) to a subject in a need thereof, sampling breath from an area in the trachea located in proximity to a distal end of the endotrachial tube (ETT) and evaluating one or more parameters related to concentration of $CO_2$ in the sampled breath.

According to some embodiments, sampling breath may include inserting a second tube into the endotrachial tube (ETT), such that the second tube reaches the area located in proximity to the distal end of the endotrachial tube (ETT), and sampling the breath through the second tube.

The endotrachial tube (ETT) may be a double lumen endotrachial tube (ETT) having a main endotrachial tube and a second endotrachial tube, wherein sampling of breath is conducted through the second endotrachial tube. The second endotrachial tube may located essentially inside the lumen of the main endotrachial tube, essentially inside the wall of the main endotrachial tube or partly in both. The second endotrachial tube is located outside the main endotrachial tube. The second endotrachial tube may have a diameter smaller than the diameter of the main endotrachial tube.

According to some embodiments, sampling may further include connecting a sampling line to a connector located at a proximal end of the second endotrachial tube.

According to some embodiments, the method may further include performing suction of fluid from the second endotrachial tube, wherein when suction is performed sampling is temporarily stopped and when sampling is performed suction is stopped.

According to some embodiments, the method may be used in children, infants and/or neonates.

According to some embodiments, the method may be used in subjects ventilated with High Frequency Ventilation (HFV), such as, but not limited to, children, infants and/or neonates.

According to some embodiments of the invention, there is provided a double lumen endotrachial tube (ETT) adapted for sampling breath from a subject for the evaluation of one or more parameters related to concentration of carbon dioxide ($CO_2$) in the sampled breath, the double lumen endotrachial tube (ETT) includes a main endotrachial tube and a second endotrachial tube, the second endotrachial tube is adapted to sample breath from a distal position in a trachea of a subject. The distal position in a trachea of a subject may include an area of the trachea located in proximity to a distal end of the endotrachial tube (ETT). The distal position in a trachea of a subject may include an area of the trachea located in proximity to a distal end of the second endotrachial tube.

According to some embodiments of the invention, there is provided a breath sampling system including a double lumen endotrachial tube (ETT) adapted for sampling breath from a subject for the evaluation of one or more parameters related to concentration of carbon dioxide ($CO_2$) in the sampled breath, the double lumen endotrachial tube (ETT) includes a main endotrachial tube and a second endotrachial tube adapted to sample breath from a trachea of a subject in an area located in proximity to a distal end of the endotrachial tube (ETT) and a breath sampling line adapted to connect to the second endotrachial tube of the double lumen endotrachial tube (ETT) through a connector.

The endotrachial tube (ETT) may be a double lumen endotrachial tube (ETT) having a main endotrachial tube and a second endotrachial tube, wherein sampling of breath is conducted through the second endotrachial tube. The second endotrachial tube may located essentially inside the lumen of the main endotrachial tube, essentially inside the wall of the main endotrachial tube or partly in both. The second endotrachial tube is located outside the main endotrachial tube. The second endotrachial tube may have a diameter smaller than the diameter of the main endotrachial tube.

The second endotrachial tube may include at a proximal end thereof a connector adapted to connect to a sampling line through a sampling opening. The connector may further include a suction port adapted to connect to a fluid suction device and/or to facilitate administration of medical agents. The connector may further include a valve, wherein when the valve is in a first position flow of sampled breath to the sampling line is allowed and the suction port is blocked and when the valve is in a second position the suction port is opened and flow of sampled breath to the sampling line is blocked.

The second endotrachial tube may include at a distal end thereof two or more openings adapted to allow flow of breath to the second endotrachial tube.

The double lumen endotrachial tube (ETT) may be adapted for use with children, infants and/or neonates.

The double lumen endotrachial tube (ETT) may be adapted for use with subjects ventilated with High Frequency Ventilation (HFV), such as, but not limited to, children, infants and/or neonates.

According to some embodiments, the one or more parameters related to concentration of $CO_2$ may include Spontaneous End tidal $CO_2$ (S-EtCO$_2$), Spontaneous final inspired $CO_2$ (S-FiCO$_2$), Continuous (Cont. $CO_2$), Diffusion $CO_2$ (DCO$_2$), density of Spontaneous breathing or any trend thereof or any combination thereof.

According to some embodiments, the endotrachial tube (ETT) may be an uncuffed endotrachial tube (ETT).

According to some embodiments of the invention, there is provided a connector adapted to connect a second endotrachial tube of a double lumen endotrachial tube (ETT) to a breath sampling line, the connector includes a connecting element adapted to connect to a second endotrachial tube of a double lumen endotrachial tube (ETT) and a sampling opening adapted to connect to a breath sampling line, wherein the second endotrachial tube is adapted to sample breath, for carbon dioxide ($CO_2$) concentration monitoring, from an area located in proximity to a distal end of the endotrachial tube (ETT).

The connector may further include a suction port adapted to connect to a fluid suction device and/or to facilitate administration of medical agents.

The connector may further include a valve, wherein when the valve is in a first position flow of sampled breath to the sampling line is allowed and the suction port is blocked and when the valve is in a second position the suction port is allowed and flow of sampled breath to the sampling line is blocked.

According to some embodiments of the invention, there is provided a method for evaluating (monitoring) carbon dioxide ($CO_2$) in breath of a subject ventilated with High Frequency Ventilation (HFV), the method includes sampling breath from a distal area of a trachea of a subject and evaluating one or more $CO_2$ related parameters. According to some embodiments, sampling may be conducted through an endotrachial tube (ETT). The endotrachial tube (ETT) may be of any form or shape, for example, sampling may be conducted through a second endotrachial tube of a double lumen endotrachial tube (ETT). According to some embodiments, particularly with HFV subjects, distal measurement(s) of $CO_2$ may be conducted without sampling, but rather by inserting (for example, but not necessarily, through an ETT) one or more $CO_2$ sensors to a trachea of a subject. The one or more $CO_2$ related parameters may include Spontaneous End tidal $CO_2$ (S-EtCO$_2$), Spontaneous final inspired $CO_2$ (S-FiCO$_2$), Continuous $CO_2$ (Cont. $CO_2$), Diffusion $CO_2$ (DCO$_2$), density of spontaneous breathing or any trend thereof or any combination thereof.

BRIEF DESCRIPTION OF FIGURES

Examples illustrative of embodiments of the invention are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures (FIGs.) are listed below.

DETAILED DESCRIPTION OF EMBODIMENTS

In the following description, various aspects of the invention will be described. For the purpose of explanation, specific configurations and details are set forth in order to provide a thorough understanding of the techniques. However, it will also be apparent to one of skill in the art that the techniques may be practiced without specific details being presented herein. Furthermore, well-known features may be omitted or simplified in order not to obscure the description(s) of the techniques.

According to some embodiments, sampling breath for CO$_2$ monitoring may be performed from a position much closer to the bronchial tube (at the lower section of the trachea) than the current sampling position. This type of CO$_2$ sampling and evaluation may also be referred to as a "distal CO$_2$ measurement". As discussed hereinabove, the current sampling configuration is problematic since it involves sampling from an area close to subject's mouth and to the proximal end of the ETT, wherein CO$_2$ is mixed with ventilated air, which eventually leads to erroneous CO$_2$ readings. It was found that sampling breath from a position closer to the bronchial tube (distal CO$_2$ measurement) may be less susceptible to air leak and/or mixing of the measured CO$_2$ with inhaled air. More particularly, sampling breath for distal CO$_2$ measurement may be performed at the distal end of the ETT which is adapted to be positioned inside the bronchial tube. According to some embodiments, sampling breath for distal CO$_2$ measurement may be performed by inserting a catheter into the ETT, wherein the catheter is adapted to sample CO$_2$. The catheter may, however, partly occlude or add resistance to the airway. According to some preferred embodiments, sampling breath for distal CO$_2$ measurement may be performed through the distal part of what is known as a double lumen Endotrachial Tube (ETT). Double lumen ETTs have been used so far as a means for suctioning and administration of surfactants and similar agents. The second (extra) lumen is typically a very small diameter tube which runs within the wall of the first lumen from about half way down to a point close to the distal exit of the ETT.

Figure 1A:
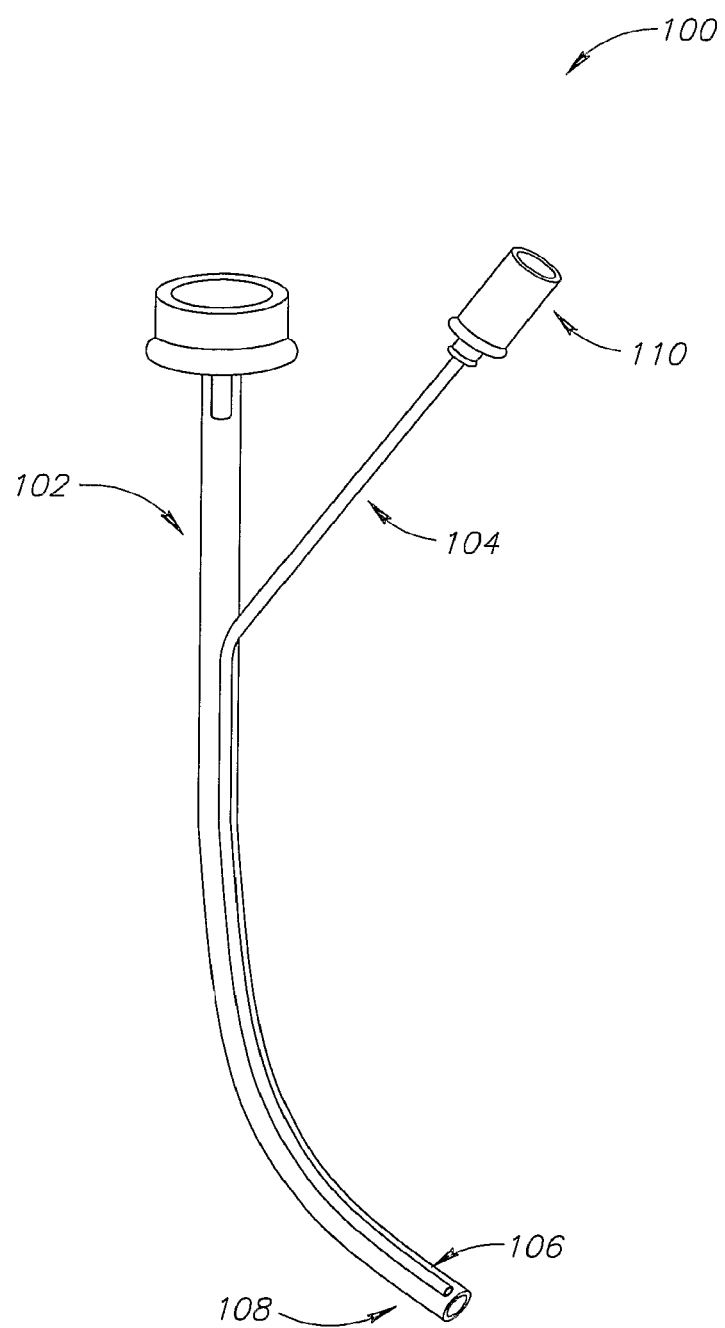
FIG. 1A-C schematically show double lumen Endotrachial Tubes (ETTs), according to some embodiments.

Reference is now made to FIG. 1A which schematically shows a double lumen Endotrachial Tube (ETT), according to some embodiments. Endotrachial Tube (double lumen ETT) 100 includes a main endotrachial tube 102 having a larger diameter and a small diameter tube 104 (for example, approximately 0.8 mm) located essentially inside and along the wall of main endotrachial tube 102. Small diameter tube 104 has a distal opening 106 a few millimeters before the distal end 108 (towards the subject's bronchial tube and lungs) of ETT 100. Small diameter tube 104 also includes, at its end opposing distal opening 106, a second opening having a connector 110, adapted to connect to or allow access to suction devices and/or to allow application of agents such as surfactants, medications or the like. According to some embodiments of the invention adapter 110 may be adapted to connect to a sampling line for sampling CO$_2$ in exhaled breath from distal end 108 of ETT 100 through small diameter tube 104. Proximal opening 130 of main endotrachial tube 102 is adapted to connect to a ventilator.

According to some embodiments, sampling breath for CO$_2$ monitoring is performed from the area of the distal end (such as distal end 108) of the double lumen EET (such as double lumen ETT 100). The sampling is performed through the small diameter tube (such as small diameter tube 104) of the double lumen ETT.

Tests clearly showed that for subjects with and without High Frequency Ventilation (HFV) (adults, children, infants and/or neonates) distal CO$_2$ measurement performed, for example through a double lumen ETT, produced a significantly better or at least comparable correlation and agreement with arterial CO$_2$. For example, better correlation was obtained between distal EtCO$_2$ (dEtCO$_2$) with arterial CO$_2$ (PaCO$_2$) than the correlation of pEtCO$_2$ measured by mainstream or sidestream capnograph sampling at the subject airway proximally with arterial CO$_2$ (PaCO$_2$).

Sampling at the distal point of the ETT in subjects and particularly in neonates has another issue: there are many fluids at the distal point. According to some embodiments, in order to solve or reduce the fluid problem and prevent them from reaching the analyzer, a fluid reducing device may be used.

The fluid reducing device may include a standard airway adapter and sampling connector to the sampling line having a stop-cock type valve allowing in its first position to sample breath and in its second position to close the sampling line and open an opening for suction of fluids from the distal section of the trachea.

According to some embodiments, it may be beneficial if the breath sampling opening of the double lumen is several millimeters inside the endotrachial main tube, with possibly several small apertures (hence, if one aperture is covered with fluids, the sampling will continue through one of the remaining openings).

Figure 1B:
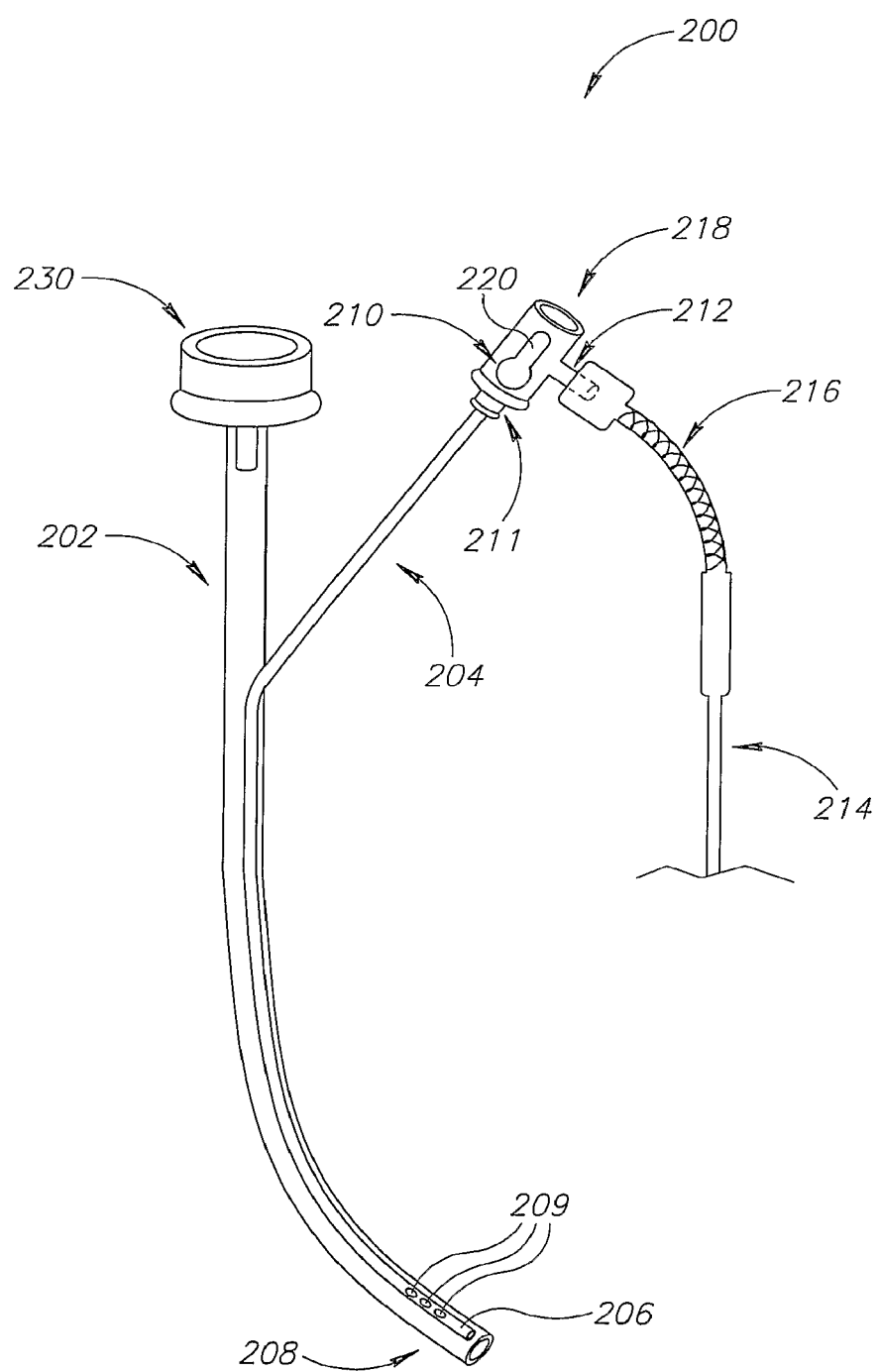

Reference is now made to FIG. 1B which schematically shows a double lumen Endotrachial Tube (ETT), according to some embodiments. Endotrachial Tube (double lumen ETT) 200 includes a main endotrachial tube 202 having a larger diameter and a small diameter tube 204 (approximately 0.8 mm) located inside and along the wall of main endotrachial tube 202. Small diameter tube 204 has a distal opening 206 a few millimeters before the distal end 208 (towards the subject's bronchial tube and lungs) of ETT 200. Distal opening 206 of small diameter tube 204 has several (in this case three) additional apertures 209. When one or more of apertures 209 is blocked with fluids, the sampling will continue through one or more of the remaining openings.

Small diameter tube 204 also includes, at its end opposing distal opening 206, a second opening having a connector 210. Connector 210 includes a connecting element 211 adapted to connect to small diameter tube 204. Connector 210 further includes a sampling opening 212 adapted to connect to a sampling line 214, optionally with drying tube 216 adapted to absorb and/or pervaporate fluids present in the sampled breath. Connector 210 also includes suction port 218 through which suction of fluids from the distal section of the trachea can be performed. Suction port 218 may also be adapted to allow application of agents such as surfactants, medications or the like. Connector 210 further includes valve 220. Valve 220 has two optional positions, a first position (as shown in FIG. 1B) allows the flow of air sampled through small diameter tube 204 to drying tube 216 and sampling line 214 and on to the analyzer (such as a capnograph). The second position (not shown) of valve 220 approximately perpendicular to the first position. In the second position, valve 220 blocks the flow of air sampled through small diameter tube 204 to drying tube 216 and sampling line 214 and allow the flow towards suction port 218.

Valve 220 (or any other valve) may be adjusted by a user to allow sampling and from time to time, as needed or every period of time, allow suction or application of medication while blocking the sampling path. Proximal opening 230 of main endotrachial tube 202 is adapted to connect to a ventilator. Valve 220 (or any other valve) may also be automatically adjusted by a controller to allow sampling and every period of time trigger suction or application of medication while blocking the sampling path. The controller may also be adapted to stop the sampling pump upon blocking the sampling line.

According to embodiments of the invention, the connector (such as connector 210) may be integrally formed with the second endotrachial tube, which may also be referred to as small diameter endotrachial tube (such as small diameter tube 204), or may be adapted to be (removably or permanently) affixed or mounted on the proximal end of the second endotrachial tube.

According to some embodiments, sampling breath for $CO_2$ monitoring is performed from the area of the distal end (such as distal end 208) of the double lumen EET (such as double lumen ETT 200). The sampling is performed through the small diameter tube (such as small diameter tube 204) of the double lumen ETT.

For clarification and the avoidance of doubt, a "double lumen ETT" or "double lumen endotrachial tube" includes an endotrachial tube with two or more lumens. The two or more lumens may have the same or different internal diameters.

The fluid reducing device may also include a drying tube, such as but not limited to a Nafion® tube or any other drying tube. In case of standard ventilation (where the waveform is analyzed) particularly in infants and neonates, it should be noted that using standard larger water traps, collectors, filters or the like may add extra dead space or minor interference to the breath flow which may effect the waveform.

In case of HFV it may be possible to add filter(s), liquid trap(s), dryer tubes or the like, since in HFV mode response time is less critical compared to standard ventilation, though its (their) size may dampen somewhat the spontaneous breaths.

According to some embodiments, one or more of the small diameter tubes of double-lumen ETTs (such as small diameter tubes 104 and 204) may be used for insertion of a sensor or a detector adapted to reach approximately the distal section of the trachea and sense (detect) breath elements such as $CO_2$. This may replace sampling or conducted in addition to sampling. Such sensor can be a chemical sensor, electronic sensor, optic sensor or any other sensor/detector. For example, the small diameter tubes of a double-lumen ETT may be adapted to receive a fiber optics adapted to transmit and return radiation (for example IR radiation at a wavelength that $CO_2$ absorbs), and thus detect one or more breath parameters (such as $CO_2$ levels or waveforms in case of standard ventilation). In another embodiment, radiation (such as light) may be emitted through the main endotrachial tube (such as main endotrachial tubes 102 and 202) in such way that light entered through the main endotrachial tube is reflected by an appropriate reflector back through an optical fiber in the small diameter tube back to an appropriate detector.

According to some embodiments, there is also provided an ETT, having a main endotrachial tube and a second endotrachial tube (optionally having a smaller diameter than the main endotrachial tube). The second endotrachial tube is located outside the main endotrachial tube (as apposed to inside of the main endotrachial tube as shown above). The distal opening of the second endotrachial tube may be in proximity to the distal opening of the main endotrachial tube but may also be shorter, such that upon insertion to the trachea, it only would only reach the cavity of the mouth for sampling exhaled air that escaped around the uncuffed ETT. This second line may also (as above) connect by a stop-cock to the main (neonatal) sampling adapter. A user could toggle between the two sampling points.

According to some embodiments, the main endotrachial tube may include, at or in proximity to its distal end, a mechanism that is adapted to open when positive pressure from a ventilator pushes in the air for ventilation, while close on exhalation. This way, the exhaled breath will be forced to return around the outside of the main endotrachial tube to be collected by the second endotrachial tube. It is noted however, that a mechanism such as mechanism 340 may apply to standard ventilation, while, in HFV where the main concept is base on diffusion, such mechanism may not be applicable.

Figure 1C:
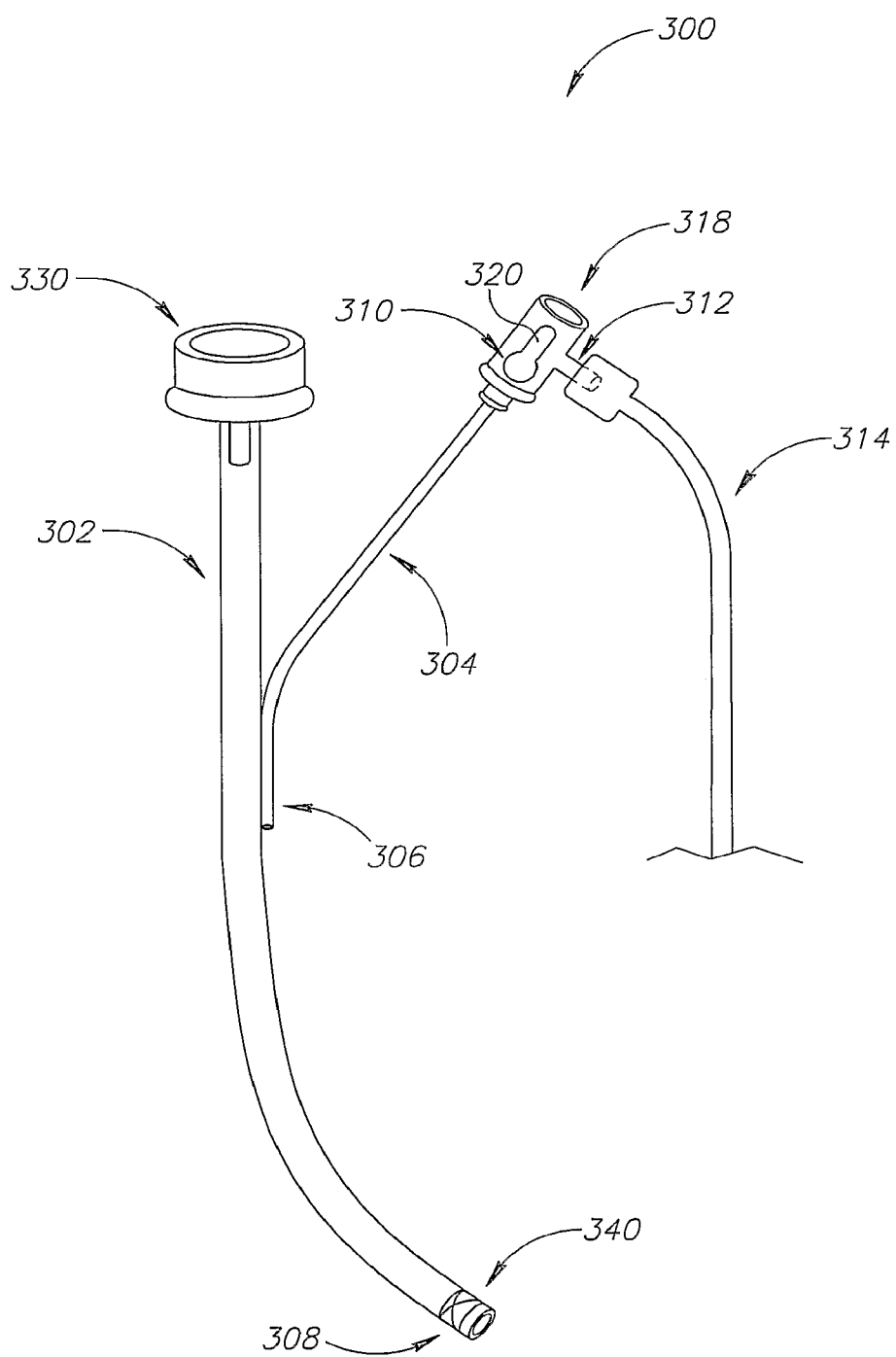

Reference is now made to FIG. 1C which schematically shows a double lumen Endotrachial Tube (ETT), according to some embodiments. Endotrachial Tube (double lumen ETT) 300 includes a main endotrachial tube 302 and a second endotrachial tube 304 located outside and along the wall of main endotrachial tube 302. Second endotrachial tube 304 has a distal opening 306 at approximately one third of the way of main endotrachial tube 302, so that upon insertion to the trachea, it only would only reach the cavity of the mouth for sampling exhaled air that escaped around uncuffed ETT 300.

Second endotrachial tube 304 also includes, at its end opposing distal opening 306, a second opening having a connector 310. Connector 310 includes a sampling opening 312 adapted to connect to a sampling line 314. Connector 310 also includes suction port 318 through which suction of fluids from the distal section of the trachea can be performed. Suction port 318 may also be adapted to allow application of agents such as surfactants, medications or the like. Connector 310 further includes valve 320. Valve 320 has two optional positions, a first position (as shown in FIG. 1C) allows the flow of air sampled through small diameter tube 304 to sampling line 314 and on to the analyzer (such as a capnograph). The second position (not shown) of valve 320 approximately perpendicular to the first position. In the second position, valve 320 blocks the flow of air sampled through small diameter tube 304 to sampling line 314 and allow the flow towards suction port 318. Valve 320 (or any other valve) may be adjusted by a user to allow sampling and from time to time, as needed or every period of time, allow suction or application of medication while blocking the sampling path. Proximal opening 330 of main endotrachial tube 302 is adapted to connect to a ventilator. Valve 320 (or any other valve) may also be automatically adjusted by a controller to allow sampling and every period of time trigger suction or application of medication while blocking the sampling path. The controller may also be adapted to stop the sampling pump upon blocking the sampling line.

Main endotrachial tube 302 also includes, in proximity to its distal end 308, a mechanism 340 that is adapted to open when positive pressure from a ventilator pushes in the air for ventilation, while close on exhalation. It is noted however, that a mechanism such as mechanism 340 may apply to standard ventilation, while, in HFV where the main concept is base on diffusion, such mechanism may not be applicable. This way, the exhaled breath will be forced to return around the outside of the main endotrachial tube to be collected by the second endotrachial tube.

According to some embodiments, a miniature nano-technology $CO_2$ sensor may be placed in the trachea through the small diameter tube of the double lumen ETT. This configuration may allow measuring the $CO_2$ in-situ. According to other embodiments, the $CO_2$ nano sensor can also be placed in any ETT not necessarily double lumen ETT. Similarly, any other sensor, such as an $O_2$ sensor may also be placed in (and/or through) the small diameter tube of the double lumen ETT or any ETT in addition or instead of the $CO_2$ nano sensor. According to some embodiments, the sensor may be disposable.

High Frequency Ventilation (HFV):

Additional or alternative embodiments of the invention are generally directed to a method and apparatus for using capnography in monitoring breath carbon dioxide ($CO_2$) in subjects, particularly, but not limited to, small children and infants, who are ventilated by High Frequency Ventilation (HFV) technique.

As discussed above when considering capnography for replacing at least some of the blood gas samples, and in general to provide continuous monitoring for HFV (such as HFOV) mode of ventilation, some difficulties arise. These difficulties include very high ventilation frequencies, lack of "clear", "textbook" breath cycle and when sampling at the standard position for capnography, either in mainstream or sidestream, the $CO_2$ concentration is much lower than what is really occurring in the lungs.

According to some embodiments of the invention, there are provided a method and apparatus for $CO_2$ sampling and monitoring in subjects (for example, but not limited to, children, infants, and neonates) ventilated by the HFV mode while overcome issues related to difficulties such as those discussed herein.

According to some embodiments of the invention, since in HFV one can expect long periods without observing typical waveforms and breath cycles, which are not the result of apnea, the platform for $CO_2$ sampling in HFV subjects should take this into account or be insensitive to such instances.

New Parameters to be Provided to the User:

This following describes, according to some embodiments of the invention, possible requirements, improvements and/or changes needed in order to provide an appropriate Capnography mode of operation with subjects ventilated with HFV.

According to some embodiments, there are provided new parameters for defining HFV mode. These parameters may optionally have their own alarm management and trend characteristics. Of course, the names given to these parameters are not binding and are only optional.

Figure 2:
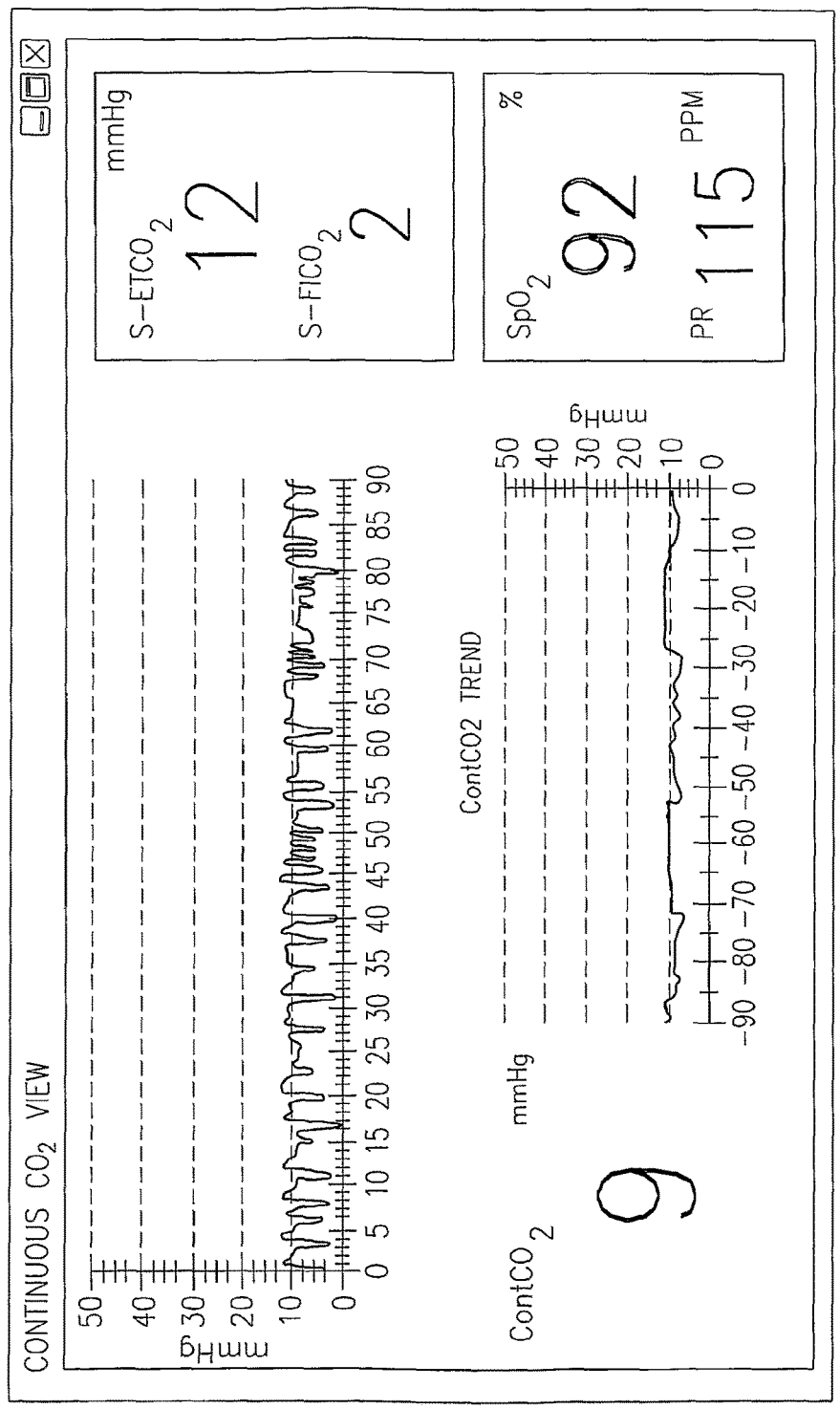
FIG. 2 shows an example of a capnograph display, according to some embodiments.

According to some embodiments, the following parameters may be defined and used for capnography in subjects ventilated with HFV. Some of these parameters may be used instead of or in addition to standard respiratory rate (RR), $EtCO_2$ parameters or other known standards.

a) Cont.$CO_2$—Continuous $CO_2$: According to some embodiments, this is a main value used in HFV capnography and can be calculated as the average $CO_2$ reading (concentration) over the last "x" seconds (which could be 5 seconds or 1 to 60 seconds or any other period), updated every "y" second ("y" could be 1 to 60 seconds or any other period). If within this period a spontaneous breath is detected or even the possible beginning of such a breath is suspected (to be defined in section "e" below), then the last Cont.$CO_2$ value could be frozen until a new period (such as, a 5-second period) has passed without any identified spontaneous breath. If the spontaneous breaths continue for more than possibly "z" seconds (such as, 60 seconds) without a "w" second (for example, 5 second) gap, the Cont. $CO_2$ value may be determined and optionally displayed as invalid (for example a dash is provided in place of the value).

b) S-$EtCO_2$—Spontaneous $EtCO_2$: If a spontaneous breath cycle (to be defined in section "e" below) is recognized (typically a result of spontaneous breathing), then, according to some embodiments, the highest $CO_2$ (concentration) value of the breath, S-$EtCO_2$ (Spontaneous $EtCO_2$), may be measures and optionally displayed. The displayed value may be the highest result that was collected over the last "m" seconds (possibly 1 to 60 seconds). Again, it may be updated every period of time (once a second for example). If for "n" seconds (for example, 20 seconds) there is no new breath, the S-$EtCO_2$ value may be determined and optionally displayed as invalid (for example a dash is provided in place of the value).

c) S-$FiCO_2$—Spontaneous fractional concentration of final inspired $CO_2$: If a breath cycle is recognized, then, according to some embodiments, the lowest $CO_2$ (concentration) value in the breath cycle (Spontaneous fractional concentration of final inspired $CO_2$, S-$FiCO_2$) may be used and the value obtained and optionally displayed being the lowest collected over the last "u" seconds (possibly 1 to 60 seconds). Again, it may be updated every period of time (once a second for example). If for "t" seconds (for example, 20 seconds) there is no new breath, the S-$EtCO_2$ value may be determined and optionally displayed as invalid (for example a dash is provided in place of the value).

d) $DCO_2$—Diffusion (gas transport coefficient) $CO_2$ $DCO_2$: This parameter may be similar to the conventional ventilation parameter that is the product of tidal volume and frequency, known as minute ventilation, which aptly describes pulmonary gas exchange. The gas transport coefficient which defines the $CO_2$ elimination correlates to the product of "oscillatory volume" squared and the frequency. For this purpose, it would be necessary to enable entering of the HFV ventilator parameters into the Capnograph.

e) Inst. $CO_2$—Instantaneous $CO_2$: a raw unprocessed measurement of $CO_2$, According to some embodiments, every period of time (for example, once every 50 msec, a $CO_2$ measurement is performed). If the measured $CO_2$ change of at least "c" mmHg ("c" can for example be between 1 and 10 mmHg) above (or below) the Cont.$CO_2$ current (latest) value and lasting for at least "k" milliseconds, msec (for example, 200 msec), a spontaneous breath is suspected. The system may trace for a peak to peak (PTP) of "c" mmHg lasting more than a minimal "k" period, for example 200 msec. During this stage the Cont.$CO_2$ value may be frozen as stated above. In case of a timeout (of for example, 3 seconds) with no "c" mmHg PTP, the PTP trace may be stopped and the Cont.$CO_2$ calculation may be resumed. A spontaneous breath is counted every 2 consecutive occurrences of "c" mmHg PTP.

f) "Low $CO_2$": Since in HFV one can expect long periods without observing a typical waveforms and breath cycles, there is no meaning to the term "apnea" or "no breath", hence the term "low $CO_2$" may be used instead.

g) High and low Cont. $CO_2$ alarms: According to some embodiments, the alarms relating to RR, high and low $EtCO_2$ may be disabled and Cont. $CO_2$ high and low may be enabled.
h) Density of spontaneous breaths: According to some embodiments the Density of spontaneous breaths may be calculated. This value may be obtained by calculating what percentage of the time the subject is spontaneously breathing
i) According to some embodiments, trends of any $CO_2$ related parameter (such as Cont. $CO_2$ may be provided and optionally presented as a graph or table that demonstrates the change of the parameter over time.
j) According to some embodiments, the Cont. $CO_2$ value may be displayed at a position where in normal mode (non-HFV) the $EtCO_2$ value is displayed. The other two parameters (S-$EtCO_2$ and $FiCO_2$) may be displayed where in normal mode (no-HFV) the RR and $FiCO_2$ are displayed.
k) According to some embodiments, the display may include two parts:
   1) A main waveform display having a sweep rate which is slower than the standard ventilation (non-HFV) generally in the range of 0.1 to 10 mm/second. This mode displays the Continuous (Cont. $CO_2$) with the sporadic spontaneous breaths superimposed on it. An example of a main waveform display can be seen in the top graph of FIG. 2, which shows an example of a capnograph display of a subject ventilated by HFV, according to some embodiments. The top graph shows the values of Cont. $CO_2$ in mmHg over time (seconds, sec). The sections of the graph having clear "dips" indicate spontaneous breathing.
   2) A display having a slower sweep rate than that of the main waveform display (section 1 hereinabove), for example in the range of 0.1 to 10 mm/min. This slower display shows the trend of the Continuous (Cont. $CO_2$), or in other words, how the Cont. $CO_2$ is changing over a period of time (for example, 90 min). This type of data may reduce or even eliminate the use of blood gas, since, for example, just by looking at it the doctor may know if the $CO_2$ level is improving since the last blood gas test obtained from the subject. An example of such a trend display can be seen in the bottom graph of FIG. 2, which shows the trend of Cont. $CO_2$ in mmHg over time (minutes, min). In addition to these graphs, values of Cont. CO2, S-$EtCO_2$, S-$FiCO_2$ as well as SpO2 and PR (pulse oximetery) may also be presented.
l) According to some embodiments, there is provided a means for manually (or automatically) entering an event mark, for example, defining a blood gas. A red spot, for example, or similar (possibly a sigh, a letter or a combination of letters such as "b.g.") may be placed on the slower trend display so that the doctor can easily see trends of $CO_2$ relative to the last blood gas time. It is preferred that one could also add the values of the blood gas in any form (values, graphical etc.) so that they can be displayed on the trend with the sampled $CO_2$ values.

According to some embodiment of the invention, the term "distal" or "distal end" may refer to a position located (or adapted to be located) towards a subject's lungs.

According to some embodiment of the invention, the term "proximal" or " proximal end" may refer to a position located (or adapted to be located) towards a subject's mouth.

According to some embodiment of the invention, the term "main endotrachial tube" may refer to a part of an endotracheal tube through which ventilation may be performed.

According to some embodiment of the invention, the term "second endotrachial tube" may refer to a part of an endotracheal tube which is not directly used for ventilation. A second endotrachial tube may be smaller in diameter than the main endotrachial tube. A second endotrachial tube may be integrally formed with the main endotrachial tube or connected thereto.

According to some embodiment of the invention, the term "sampling line" or "breath sampling line" may refer to any type of tubing(s) or any part of tubing system adapted to allow the flow of sampled breath, for example, to an analyzer, such as a capnograph. The sampling line may include tubes of various diameters, adaptors, connectors, valves, drying elements (such as filters, traps, trying tubes, such as Nafion® and the like).

EXAMPLES

Example 1

Correlation between Sampling through a Double Lumen ETT and Blood Gas

Study Design

A prospective observational study was conducted at Bnai-Zion Medical Center, Haifa, Israel. Infants were connected simultaneously to proximal and distal $EtCO_2$ monitors, and the measurements were compared to $PaCO_2$ drawn for patient care. Measurements of distal $EtCO_2$ ($dEtCO_2$) were not used for patients' clinical care. The study was approved by the institutional review board. All the parents signed an informed consent prior to participating in the study.

The primary outcome measure was to evaluate the accuracy and the correlation of Microstream $dEtCO_2$ with the gold standard of $PaCO_2$. The secondary outcome measure was to compare these findings to the more standard and commonly used method of mainstream $pEtCO_2$.

Study Population

Included in the study were all intubated infants in the NICU during the study period, who had the double lumen endotracheal tubes (ETT) and that their parents signed an informed consent. Excluded were infants with a single lumen endotracheal tube.

All infants who needed an ETT were intubated in the delivery room or in the NICU by a double lumen tube (Uncuffed Tracheal Tube, Mallinckrodt Inc., Chih, Mexico). This ETT has an extra small lumen for administration of exogenous surfactant or for measurements of distal pressures close to the carina. In this study this side port was used to measure dEtCO2 only.

Intubated infants were monitored by the two capnograms simultaneously. The side-stream $dETCO_2$ was measured distally by a Microstream capnograph via a Microstream cannula (Oridion Medical Inc., Needham, Mass.). The mainstream $pETCO_2$ was measured via capnogram connected to the proximal end of the ETT (Philips IntelliVue patient monitor, Capnography Extension M3014A, Philips, Boeblingen, Germany). Readings from the two methods were charted at the time of blood sampling for routine patient care via an indwelling arterial line and compared to $PaCO_2$ level (Omni AVL, Roche Diagnostic Gmbh, Graz, Austria). Before each blood sampling it was assured that an adequate reading of $pEtCO_2$ and a reliable waveform on the Microstream capnograph (continuous steady waveform of expired $CO_2$ throughout the ventilatory cycle), and cleared secretions from the side port of the ETT for $dEtCO_2$ measurement (by inserting 5 ml of air). Microstream cannulas blocked by secretions were replaced as needed.

Data on the patients' characteristics, type of their pulmonary or cardiac disease and the severity of pulmonary disease (by oxygenation index defined as fractional inspired of oxygen [$FiO_2$] X mean airway pressure/$PaO_2$ and by the level of ventilation perfusion mismatch assessed by $PaO_2$/$PAO_2$ ratio) was collected. Severe lung disease was defined as: $PaO_2$/$PAO_2$ ratio<0.3 (18, 19) or OI>10; mild-moderate lung disease: $PaO_2$/$PAO_2$ ratio>0.3 and OI<10 ($PAO_2$ was calculated by: $FiO_2$ X [Barometric pressure−47]−$PaCO_2$/0.8]. $PaCO_2$ was assumed the same as alveolar $PACO_2$.

A bias ≤5 mmHg was considered a low bias and >5 mmHg a high bias (9, 10).

The consistency of $EtCO_2$ monitoring (proximal and distal) within each patient was assessed by examining the relationship between the change in $PaCO_2$ and the change $EtCO_2$ in consecutive samples.

Statistical Analysis

The correlation of distal and proximal $EtCO_2$ and $PaCO_2$ was evaluated by linear regression analysis and assessed the agreement between these measurements (bias [mean difference] and precision [standard deviation of the differences]) by the Bland-Altman technique (22).

The correlation between the changes in $PaCO_2$, and the simultaneous changes in proximal and distal $EtCO_2$ were evaluated for consecutive measurements within each patient by linear regression analysis.

Level of significance was set at p<0.05. SigmaStat version 2.03, Chicago, Ill. and the Minitab version 12.23, State College, Pa. statistical softwares were employed.

Results

Twenty-seven infants participated in the study and 222 measurements of distal $EtCO_2$ and 212 of proximal $EtCO_2$ were analyzed. In 10 infants proximal $EtCO_2$ could not be measured continuously. Table 1 shows the characteristics of the patients who participated in the study.

TABLE 1

Patients' characteristics (n = 27)

| | Median | Range |
|---|---|---|
| Gestational age (weeks) | 32.5 | (24.8-40.8) |
| Birth weight (g) | 1835 | (490-4790) |
| Age of enrolment (days) | 1 | (1-26) |
| Number of observations | 8 | (1-24) |
| pH | 7.34 | 6.5-7.5 |
| $FiO_2$* | 0.31 | 0.21-1.00 |
| $PaO_2$/$PAO_2$ ratio** | 0.50 | 0.06-2.38 |
| Oxygenation index (OI)*** | 3.29 | 0.63-23.0 |
| Primary diagnosis (n = 27 infants) | | |
| Respiratory distress syndrome | | 19 |
| Tracheo-esophageal fistula and esophageal atresia | | 3 |
| Pneumonia | | 1 |
| Primary pulmonary hypertension | | 1 |
| Meconium aspiration syndrome | | 1 |
| Hypoxic ischemic encephalopathy | | 1 |
| Necrotizing enterocolitis | | 1 |

*$FiO_2$ Inspired oxygen fraction;
**$PaO_2$/$PAO_2$ alveolar/arterial oxygen tension ratio;
***OI = $FiO_2$ × mean airway pressure/$PaO_2$ The median (range) levels of $PaCO_2$, $dEtCO_2$, $pEtCO_2$ were 46.3 (24.5-99.7) mmHg, 46.0 (20.0-98.0) mmHg, and 37.0 (12.0-71.0) mmHg, respectively.

Figure 3A:
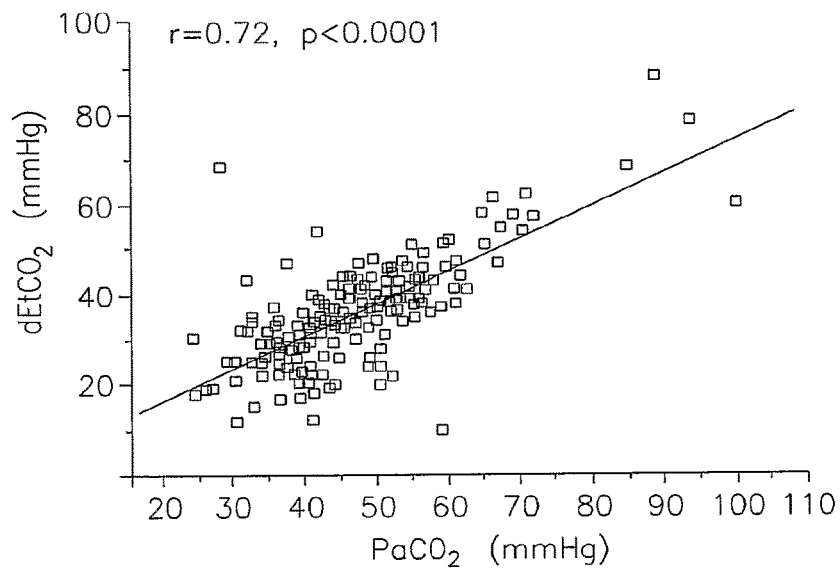
FIG. 3 A and B show the linear correlation between distal EtCO$_2$ (dEtCO$_2$) (A) and proximal EtCO$_2$ (pEtCO$_2$) (B) and arterial $CO_2$ (PaCO$_2$), according to some embodiments.
Figure 3B:
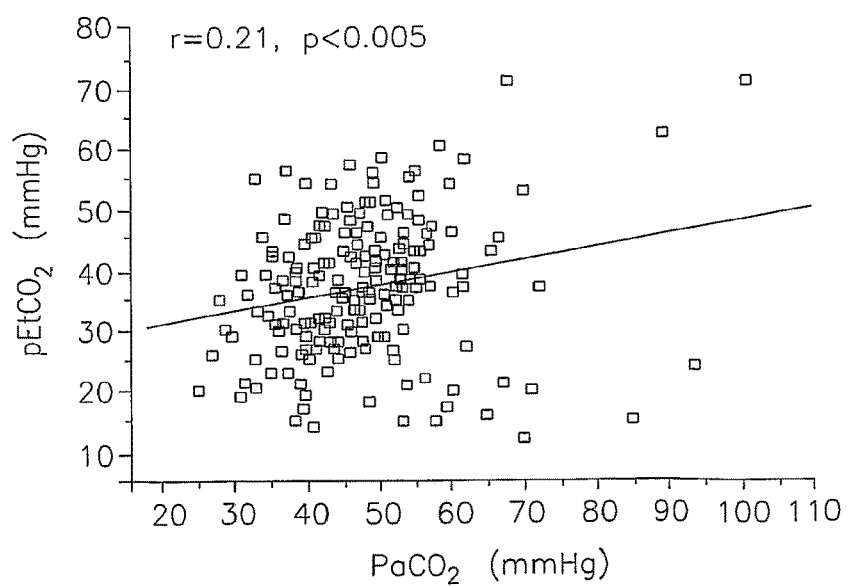

FIGS. 3A and B show the linear correlation between distal $EtCO_2$, $dEtCO_2$ (A) and proximal $EtCO_2$, $pEtCO_2$ (B) with arterial $PCO_2$, according to some embodiments. While the correlation coefficient (r) of $dEtCO_2$ and $PaCO_2$ was adequate (r=0.72, p<0.001), the r of the $pEtCO_2$ was poor (r=0.21, p=0.002).

Figure 4A:
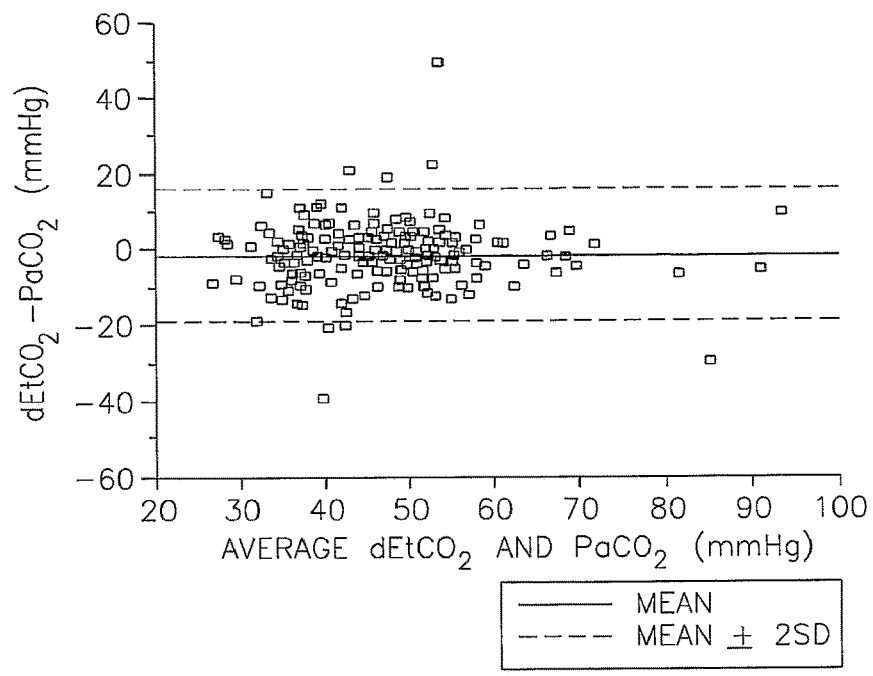
FIGS. 4A and B present the Bland-Altman plots of the differences between distal EtCO$_2$ (dEtCO$_2$) (A) and proximal EtCO$_2$ (pEtCO$_2$) (B) and arterial $CO_2$ (PaCO$_2$), according to some embodiments.
Figure 4B:
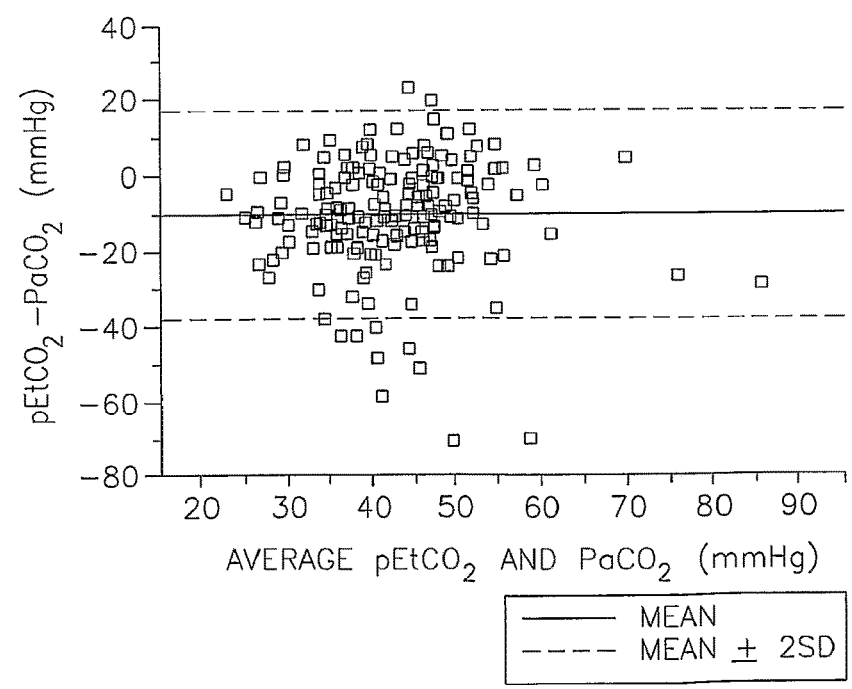

FIGS. 4A and B present the Bland-Altman plots of the differences between distal $EtCO_2$, $dEtCO_2$ (A) and proximal $EtCO_2$, $pEtCO_2$ (B) and arterial $CO_2$, $PaCO_2$, according to some embodiments. The mean difference (bias) and the standard deviation of the differences (precision) for the $dEtCO_2$ were −1.5±8.7 mmHg , and for the $pEtCO_2$ −10.2±13.7 mmHg, respectively. The correlating medians (25 and 75 percentiles) were: −1.1 (−5.6 and 2.7) and −10.3 (−16.0 and −0.8), respectively. Although both, distal and proximal $EtCO_2$ levels underestimated the $PaCO_2$ level, $dEtCO_2$ was more accurate than $pEtCO_2$ as a non-invasive measure of $PaCO_2$.

$dEtCO_2$ (21 samples) remained reliable as a measure of $PaCO_2$, while $pEtCO_2$ (19 samples) was distorted on the high range of $PaCO_2$ levels (≥60 mmHg) (r=0.77, p<0.001 and r=0.21, p=0.38; bias±precision: −4.8±7.9 and −33.3±20.0; respectively).

Table 2 shows the effect of the severity of pulmonary disease (assessed by $PaO_2$/$PAO_2$ ratio or by OI) on the accuracy of distal and proximal $EtCO_2$ readings. It was found that $dETCO_2$ still correlated with $PaCO_2$, but its bias increased with the severity of pulmonary disease.

TABLE 2

Relation between $EtCO_2$ values and severity of lung disease

| | Mild to Moderate Mean (SD); r, p value | Severe lung disease Mean (SD); r, p value |
|---|---|---|
| $PaO_2$/$PAO_2$ ratio | >0.3 (n = 168) | ≤0.3 (n = 63) |
| P (Et-a distal) $CO_2$ | −0.24 ± 7.3; 0.74, <0.001 | −4.2 ± 10.5; 0.64, <0.001 |
| P (Et-a proximal) $CO_2$ | −9.1 ± 14.0; 0.07, =0.34 | −12.5 ± 12.5; 0.35, <0.01 |
| Oxygenation index | <10 (n = 216) | ≥10 (n − 16) |
| P (Et-a distal) $CO_2$ | −0.7 ± 8.2; 0.69, <0.001 | −9.0 ± 8.1; 0.77, <0.001 |
| P (Et-a proximal) $CO_2$ | −9.8 ± 13.9; 0.13, =0.07 | −13.0 ± 9.8; 0.52, =0.054 |

All $CO_2$ levels in mmHg

The changes in $PaCO_2$, and the simultaneous changes in proximal and distal $EtCO_2$ were evaluated for consecutive measurements within each patient. The mean changes in $PaCO_2$ were 0.12±9.3 mmHg and in $dEtCO_2$ 0.90±10.8 mmHg, with r between the changes of 0.49, p<0.001. Mean change in $pEtCO_2$ was −0.02±8.5 mmHg, with r of 0.17, p<0.05, compared to the simultaneous changes in $PaCO_2$.

This study shows that the novel method of measuring dEtCO2 through a double-lumen ETT had a better correlation and agreement with $PaCO_2$ when compared to the standard mainstream $pEtCO_2$ method in neonates. The accuracy of $dEtCO_2$ decreased but it remained a reliable measure of $PaCO_2$ even in the high range of $PaCO_2$ (≥60 mmHg) or in conditions of severe lung disease.

It was found that $dEtCO_2$ was an accurate and reliable non-invasive method for estimating $PaCO_2$. It had a good correlation with $PaCO_2$ (n=222, r=0.72, p<0.001), which was slightly lower compared to mainstream $pEtCO_2$ (n=411, r=0.83, p<0.001) as previously reported for NICU infants by Rozycki et at (10). The bias reported for $dEtCO_2$ (−1.5±8.7 mmHg) was even smaller than that reported by Rozycki et at for mainstream $pEtCO_2$ (−6.9±6.9 mmHg), and was well <5 mmHg, which is considered within the good agreement range (9, 10). In the study, the correlation and the agreement of $dEtCO_2$ with $PaCO_2$ were better than those for mainstream $pEtCO_2$. Several investigators reported similar results for distal and proximal sidestream $EtCO_2$ (17, 18) while others reported comparable accuracy of distal and proximal mainstream $EtCO_2$ (11). However, neither of these studies measured $dEtCO_2$ by a double lumen ETT, nor did they use the Microstream technique. The study results regarding the mainstream $pEtCO_2$ should be interpreted with caution, as others reported better results for that method (10). This could result from different conditions in the different studies reflected by mixture of patients, severity of their lung disease, levels of leak around the ETT, and instrumentation used for measurements.

Severity of disease was reported to affect the accuracy of capnometry in several studies. The more severe the ventilation perfusion mismatch, the higher the difference between $EtCO_2$ and $PaCO_2$ (9, 20). Parenchymal lung disease with ventilation perfusion mismatching is a common feature in NICUs. Sivan et at (20) reported that $PaO_2/PAO_2$ ratio >0.3 was associated with better agreement between $EtCO_2$ and $PaCO_2$ and Hagerty et at (9) found a higher gradient between $EtCO_2$ and $PaCO_2$ when comparing newborn with pulmonary disease and those receiving mechanical ventilation for non-pulmonary conditions. Different results were reported by other investigators. Tingay et at (19) found that the $EtCO_2$ bias was independent of severity of lung disease and Rozycki et at (10) reported that measures of degree of lung disease (ventilation index and oxygenation index) had small influence on the degree of bias. In the study the agreement of $dEtCO_2$ and $PaCO_2$ decreased, but the bias in patients with $PaO_2/PAO_2$ ratio<0.3 remained <5 mmHg. It was assessed whether the level of $PaCO_2$ affected the accuracy of $EtCO_2$ readings, and found it to affect the $pEtCO_2$ much more than the $dEtCO_2$, which remained with adequate agreement with the $PaCO_2$. Rosycki et at did not find that the accuracy of $pEtCO_2$ was affected by the $PaCO_2$ level (10). The findings suggest that $dEtCO_2$ as evaluated in the study could be used as a reliable non-invasive method for $PaCO_2$ assessment in the full spectrum of NICU patients.

Although the Microstream sidestream capnography was used previously in (only) two studies in newborns (9, 19), this is the first time a double lumen ETT is used for the disclosed perpose, which allowed continuous measurement of $dEtCO_2$ via its extra lumen.

The intention of the Microstream technique is to improve the accuracy of sidestream capnomtery which is traditionally considered less accurate than the mainstream capnometry (11, 13, 14, 15, 16). Microstream capnography employs a sampling flow rate of 50 ml/min, approximately one third of that used by previous studies with conventional sidestream systems. This low flow rate eliminates the competition for tidal volume and also decreases condensation within the system. Because of the highly $CO_2$—specific infrared source (emission that exactly matches the absorption spectrum of the $CO_2$ molecule), the sample cell utilizes a much smaller volume (15 µl) that permits a low flow rate without compromising response rate or accuracy. These features preserve accuracy by preventing mixing of the small inspiratory and expiratory volumes observed in newborns, while rapid response time is maintained by laminar gas flow throughout the breathing circuit (22). The new low-flow sidestream capnograph (Oridion Medical Inc., Needham, Mass., USA) was tested when connected to the side port of the proximal ETT by Hagerty et at (9), and they reported a gradient of 3.4±2.4 mmHg in ventilated infant without pulmonary disease and 7.4±3.3 in those with pulmonary disease. Tingay et at (19) also used the Microstream technique (Agilent Microstream system, Andover, Mass., USA) for monitoring $pEtCO_2$ in infants during neonatal transport. They reported that the $pEtCO_2$ had a linear relation with $PaCO_2$ but had an unacceptable underestimation of $PaCO_2$ (8.2±5.2 mmHg), and did not trend reliably over time within an individual patient. In the study, using the Microstream technique (Oridion Medical Inc., Needham, Mass., USA), but measuring $dEtCO_2$ via the side port of the double lumen ETT, the agreement with $PaCO_2$ improved, in infants with both mild and severe pulmonary disease (−0.24±7.3, and −4.2±10.5; respectively). The improvement could be related to distal measurements of $EtCO_2$. This technique which measures $EtCO_2$ close to the carina, may be less affected by the ventilatory circuit flow and leaks around the uncuffed ETTs used in neonates and thus better represent the accurate $PaCO_2$. $dEtCO_2$ as opposed to $pEtCO_2$ are not affected by flow sensors which are commonly used nowadays with the new ventilators (flow sensors in the study prevented the use of $pEtCO_2$ in few infants because of inadequate continuous measurements).

The novel method of measuring $dEtCO_2$ via a double-lumen endotracheal tube was found to have good correlation and agreement with $PaCO_2$, and is thus a reliable in conditions of severe lung disease. $dEtCO_2$ was more accurate than the standard mainstream $pEtCO_2$ method as assessed in the study. $EtCO_2$ does not replace $PaCO_2$, but may be useful for trending and for real time continuous screening of abnormal $PaCO_2$ levels. As noninvasive $CO_2$ monitoring may be of importance for the short and long term outcome of intubated neonates, and as the current available methods are limited, medical teams should consider the use of this non-invasive method of assessing $PaCO_2$ in NICUs.

Example 2

Correlation between Sampling through a Double Lumen ETT and Blood Gas in Patients Ventilated by HFV Eight patients ventilated by HFV were tested, comparing mainstream capnography to Microstream capnography wherein the sampling line is connected to the distal end of a double lumen ETT. In most of the cases 2.5 mm ETT (internal diameter of the main endotracheal tube) were used. Correlation to blood gas was used as the reference.

Figure 5:
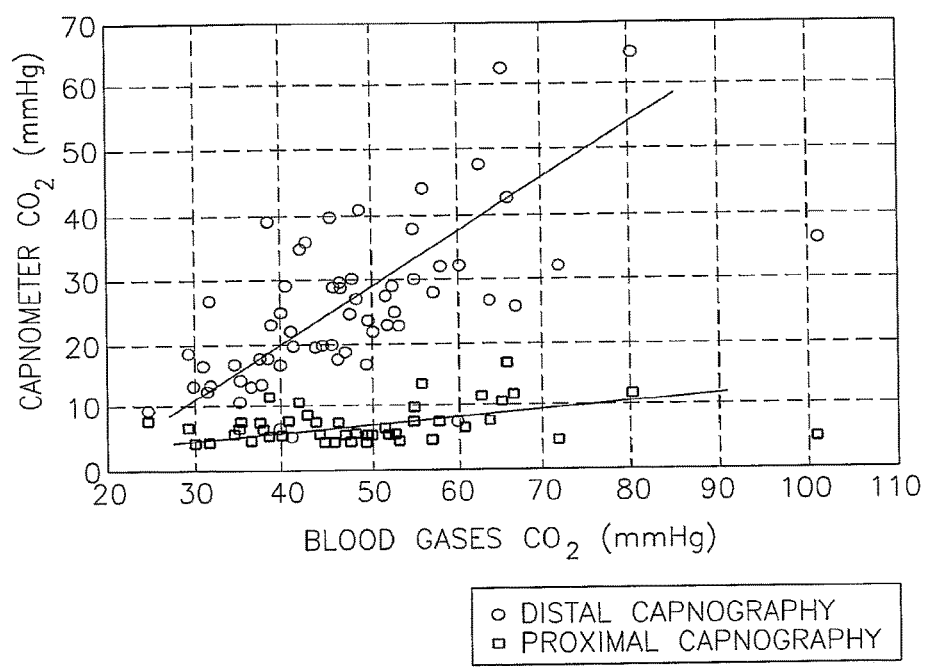
FIG. 5 shows the linear correlation between distal EtCO$_2$ (dEtCO$_2$) and arterial CO$_2$ (PaCO$_2$) in subjects ventilated with High Frequency Ventilation (HFV), according to some embodiments.

Continuous distal sampling with minor liquid issues was conducted (without having to toggle). Further, two Nafion® pieces were placed along the sampling line, one next to the double lumen connector, and one about 40 cm down the line. The second Nafion® was used since often the neonate is in a controlled humidified incubator, and hence one Nafion® must be placed also in the outside environment. The results are described in FIG. 5 which shows the linear correlation between distal $EtCO_2$, $dEtCO_2$ and arterial $CO_2$, $PaCO_2$ in patients ventilated with High Frequency Ventilation (HFV), according to some embodiments. The correlation between $dEtCO_2$ and $PaCO_2$ was shown to be much better than the correlation between $pEtCO_2$ and $PaCO_2$.

In the description and claims of the application, each of the words "comprise" "include" and "have", and forms thereof, are not necessarily limited to members in a list with which the words may be associated.

The invention has been described using various detailed descriptions of embodiments thereof that are provided by way of example and are not intended to limit the scope of the invention. The described embodiments may comprise different features, not all of which are required in all embodiments of the invention. Some embodiments of the invention utilize only some of the features or possible combinations of the features. Variations of embodiments of the invention that are described and embodiments of the invention comprising different combinations of features noted in the described embodiments will occur to persons with skill in the art. It is intended that the scope of the invention be limited only by the claims and that the claims be interpreted to include all such variations and combinations.

REFERENCES, INCLUDED HEREIN BY REFERENCE IN THEIR ENTIRETY

1. Garland J S, Buck R K, Allred E N, Leviton A. Hypocarbia before surfactant therapy appears to increase bronchopulmonary dysplasia risk in infants with respiratory distress syndrome. *Arch Pediatr Adolesc Med* 1995; 149 (6):617-22
2. Fujimoto S, Togari H, Yamaguchi N, Mizutani F, Suzuki S, Sobajima H. Hypocarbia and cystic periventricular leukomalacia in premature infants. *Arch Dis Child* 1994; 71(2):F107-10
3. Wyatt J S, Edwards A D, Cope M, Delpy D T, McCormick D C, Potter A, Reynolds E O. Response of cerebral blood volume to changes in arterial carbon dioxide tension in preterm and term infants. *Pediatr Res* 1991; 29(6):553-7
4. Van de Bor M, Van Bel F, Lineman R, Ruys J H. Perinatal factors and periventricular-intraventricular hemorrhage in preterm infants. *Am J Dis Child* 1986; 140(11):1125-30
5. Strauss R G. Transfusion therapy in neonates. *Am J Dis Child* 1991; 145(8):904-11. Review.
6. Bhende M S. End-tidal carbon dioxide monitoring in pediatrics—clinical applications. *J Postgrad Med* 2001; 47(3):215-8. Review
7. Wyllie J, Carlo W A. The role of carbon dioxide detectors for confirmation of endotracheal tube position. *Clin Perinatol* 2006; 33(1):111-9, vii. Review
8. Current limitations of volumetric capnography in surfactant-depleted small lungs. *Pediatr Crit Care Med* 2004; 5(1):75-80
9. Hagerty J J, Kleinman M E, Zurakowski D, Lyons A C, Krauss B. Accuracy of a new low-flow sidestream capnography technology in newborns: a pilot study. *J Perinatol* 2002; 22(3):219-25
10. Rozycki H J, Sysyn G D, Marshall M K, Malloy R, Wiswell T E Mainstream end-tidal carbon dioxide monitoring in the neonatal intensive care unit. *Pediatrics* 1998; 101(4 Pt 1):648-53
11. McEvedy B A, McLeod M E, Kirpalani H, Volgyesi G A, Lerman J. End-tidal carbon dioxide measurements in critically ill neonates: a comparison of side-stream and mainstream capnometers. *Can J Anaesth* 1990; 37(3): 322-6
12. Wu C H, Chou H C, Hsieh W S, Chen W K, Huang P Y, Tsao P N. Good estimation of arterial carbon dioxide by end-tidal carbon dioxide monitoring in the neonatal intensive care unit. *Pediatr Pulmonol* 2003; 35(4):292-5
13. Pascucci R C, Schena J A, Thompson J E. Comparison of sidestream and mainstream capnometer in infants. *Crit Care Med* 1989; 17: 560-562
14. Hand I L, Shepard E K, Krauss A N, Auld P A. Discrepancies between transcutaneous and end-tidal carbon dioxide monitoring in the critically ill neonate with respiratory distress syndrome. *Crit Care Med* 1989; 17(6): 556-9
15. Kirpalani H, Kechagias S, Lerman J. Technical and clinical aspects of capnography in neonates. *J Med Eng Technol* 1991; 15:154-61
16. Schieber R A, Namnoum A, Sugden A, Saville A L, On R A. Accuracy of expiratory carbon dioxide measurements using the coaxial and circle breathing circuits in small subjects. *J Clin Monit* 1985; 1:149-55
17. Badgwell J M, McLeod M E, Lerman J, Creighton R E. End-tidal PCO2 measurements sampled at the distal and proximal ends of the endotracheal tube in infants and children. *Anesth Analg* 1987; 66(10):959-64
18. McEvedy B A, McLeod M E, Mulera M, Kirpalani H, Lerman J. End-tidal, transcutaneous and arterial CO2 measurements in critically ill neonates: a comparative study. *Anesthesiology* 1988; 69:112-6.
19. Tingay D G, Stewart M J, Morely C J. Monitoring of end tidal carbon dioxide and transcutaneous carbon dioxide during neonatal transport. *Arch Dis Child Fetal Neonatal Ed* 2005; 90:F523-F526.
20. Sivan Y, Eldadah M K, Cheah T E, Newth C J. Estimation of arterial carbon dioxide by end-tidal and transcutaneous PCO2 measurements in ventilated children. *Pediatr Pulmonol* 1992; 12:53-7
21. Bland J M, Altman D G. Statistical methods for assessing agreement between two methods of clinical measurement. *Lancet* 1986; 1:307-10
22. Colman Y, Krauss B. Microstream capnography technology: a new approach to an old problem. *J Clin Monit* 1999; 15:403-9
23. Palmisiano B W, Severinghaus J W. Transcutaneous $PCO_2$ and $PO_2$: a multicenter study of accuracy. *J Clin Monitor* 1990; 6:189-195
24. Rennie J M. Transcutaneous carbon dioxide monitoring. *Arch Dis Child* 1990; 65:345-346

What is claimed is:

1. A method for detecting spontaneous breaths in a subject ventilated with high frequency ventilation (HFV) using a capnograph, the method comprising:
    ventilating the subject with HFV, wherein the ventilating comprises providing respiratory gas through a ventilation lumen of an endotracheal tube (ETT);
    monitoring a level of carbon dioxide ($CO_2$) in a breath of the subject, wherein the monitoring comprises:
        repeatedly sampling breath from a distal area of a trachea of the subject through a sampling lumen of the endotracheal tube (ETT) over a rolling time window during ventilation, wherein the sampling lumen is separate from the ventilation lumen and comprises a distal opening that is open to the distal area and proximate to a distal end of the ETT; thereby substantially preventing mixing of the sampled breath with inhaled air;
        measuring a $CO_2$ related parameter of the sampled breath via a $CO_2$ sensor coupled to the sampling lumen to determine $CO_2$ concentrations of each sampled breath at a plurality of time points in the rolling time window based on the measured $CO_2$ related parameter;
    using a processor of the capnograph to determine over the rolling time window:
        a continuous $CO_2$ (Con.$CO_2$) value in the sampled breath using an average of the $CO_2$ concentrations; and
        an instantaneous $CO_2$ concentration value in the sampled breath using a $CO_2$ concentration from a single time point during the rolling time window;

identifying, using the processor, spontaneous breathing when the instantaneous $CO_2$ concentration measured deviates from the determined $Con.CO_2$ value by a predetermined threshold value;

displaying the $Con.CO_2$ value and the identified spontaneous breathing on a display; and providing instructions to stop updating the displaying of the $Con.CO_2$ value when the spontaneous breathing is identified and continue displaying the $Con.CO_2$ value associated with the identified spontaneous breathing until no spontaneous breathing is identified.

2. The method of claim 1, wherein a spontaneous breath is identified when the instantaneous $CO_2$ concentration deviates from the $Con.CO_2$ value by the predetermined threshold value for a predetermined period of time.

3. The method of claim 1, further comprising computing a density of spontaneous breaths.

4. The method of claim 1, wherein the time window is continuously updated.

5. The method of claim 1, wherein the subject is a child, an infant, and/or a neonate.

6. The method of claim 1, wherein the $Con.CO_2$ value is displayed graphically and wherein the identified spontaneous breathing is superimposed on the graphically displayed $Con.CO_2$ value.

7. The method of claim 6, wherein the $Con.CO_2$ value is displayed as a waveform having a sweep rate slower than a rate of HFV.

8. The method of claim 1, wherein the sampling lumen is coupled to the $CO_2$ sensor via a valve, and comprising providing instructions to a controller to open the valve at the plurality of time points.

9. The method of claim 8, comprising providing instructions to the controller to close the valve when the spontaneous breathing is identified and comprising freezing determining the $Con.CO_2$ value when the spontaneous breathing is identified.

10. The method of claim 1, wherein the $CO_2$ sensor is an optical sensor, and wherein the $CO_2$ concentrations are determined based on detected light returned through the sampling lumen.

11. The method of claim 1, displaying an error message associated with the $Con.CO_2$ value or stopping display of the $Con.CO_2$ value when the spontaneous breathing continues for greater than a predetermined time.

* * * * *